United States Patent [19]

Inoue et al.

[11] Patent Number: 4,531,009

[45] Date of Patent: Jul. 23, 1985

[54] PROCESS FOR PREPARING α,ω-BIS(2-CHLOROPHENOXY)ALKANE-4,4'-DICARBOXYLIC ACID OR ITS LOWER ALKYL ESTER

[75] Inventors: Toshihide Inoue, Ichinomiya; Hideo Komatsu, Ehime, both of Japan

[73] Assignee: Toray Industries, Inc., Tokyo, Japan

[21] Appl. No.: 537,393

[22] PCT Filed: Jan. 28, 1983

[86] PCT No.: PCT/JP83/00024

§ 371 Date: Sep. 12, 1983

§ 102(e) Date: Sep. 12, 1983

[87] PCT Pub. No.: WO83/02609

PCT Pub. Date: Aug. 4, 1983

[30] Foreign Application Priority Data

Jan. 29, 1982 [JP] Japan .................................. 57-11863
Oct. 4, 1982 [JP] Japan .................................. 57-173323

[51] Int. Cl.$^3$ ............................................. C07C 69/76
[52] U.S. Cl. ......................................... 560/65; 562/474
[58] Field of Search ........................... 560/65; 562/474

[56] References Cited

U.S. PATENT DOCUMENTS 3,426,035   2/1969   Bremmer ............................... 560/65

FOREIGN PATENT DOCUMENTS 47-15338   5/1972   Japan ..................................... 560/65
47-27089   7/1972   Japan ..................................... 560/65
9102639    9/1974   Japan ..................................... 560/65

Primary Examiner—Paul J. Killos
Attorney, Agent, or Firm—Austin R. Miller

[57] ABSTRACT

A process for producing an α,ω-bis(2-chlorophenoxy)alkane-4,4'-dicarboxylic acid or its ester, that has a high Young's modulus and that is useful as a material for polyesters capable to form self-extinguishing fibers and films. Thus α,ω-bis(2-chlorophenoxy)alkane-4,4'-dicarboxylic acid or its ester is obtained by reacting α,ω-bis(phenoxy)alkane-4,4'-dicarboxylic acid or its ester with chlorine in the presence of a solvent selected from the group consisting of lower fatty acid having 2 to 6 carbon atoms, hydrocarbon chloride having 1 to 8 carbon atoms, and carbon chloride having 1 to 2 carbon atoms, in high yield.

8 Claims, No Drawings

PROCESS FOR PREPARING α,ω-BIS(2-CHLOROPHENOXY)ALKANE-4,4'-DICARBOXYLIC ACID OR ITS LOWER ALKYL ESTER

FIELD OF THE INVENTION

This invention relates to a process for preparing α,ω-bis(2-chlorophenoxy)alkane-4,4'-dicarboxylic acid or its lower alkyl ester in high yield.

DESCRIPTION OF THE PRIOR ART

It is known that a polyester is obtained by condensation reaction of α,ω-bis(2-chlorophenoxy)alkane-4,4'-dicarboxylic acid or its derivatives represented by the following formula

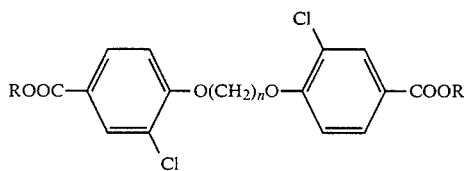

(wherein R denotes a radical selected from hydrogen and lower alkyl radical, n denotes an integer of 2,4, and 6),
and an alkylene glycol (Published Examined Japanese Patent Application Nos. 1795/74 and 13238/74).

In the prior art, the above mentioned chlorinated dicarboxylic acid was prepared by a process comprising chlorinating p-hydroxy benzoic acid or its ester, and reacting the resulting product with α,ω-dihalogeno polymethylene(Published Examined Japanese Patent Application No. 11899/75).

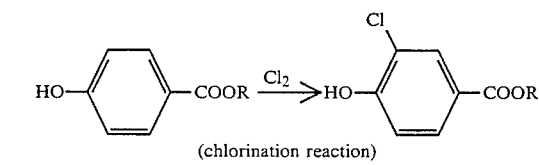
(chlorination reaction)

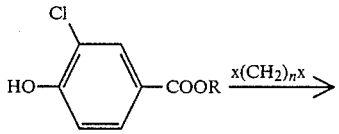

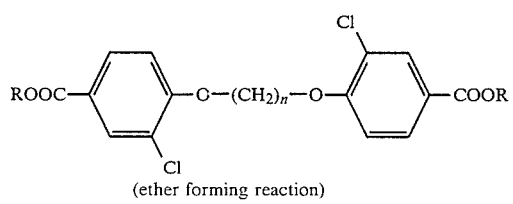
(ether forming reaction)

However, in the ether forming reaction of this prior art, when α,ω-dibromo polymethylene is used as a reactant, the yield is 60 to 75 percent (refer to the Examples of Published Examined Japanese Patent Application No. 11899/75), but the following problem has existed. That is, since NaBr which is by-produced in the reaction causes the severe corrosion of the metal, the usual reaction vessel made of stainless steel was not able to be used.

Moreover, α,ω-dibromo polymethylene is expensive. On the other hand, when α,ω-dichloro polymethylene is used as a starting material, the yield is at most 40 percent (refer to Comperative Examples in the present invention). Therefore, since the total yields of the halogenation reaction and the ether forming reaction become even lower, the preparation method is disadvantageous to adapt for industrial use.

Accordingly, the object of the invention is to provide an economical process for preparing pure α,ω-bis(2-chlorophenoxy)alkane-4,4'-dicarboxylic acid or its lower alkyl ester in high yield.

The foregoing object is effectively accomplished by heating p-hydroxybenzoic acid or its lower alkyl ester with alkylene dichloride, to obtain α,ω-bis(phenoxy)alkane-4,4'-dicarboxylic acid or its lower alkyl ester (ether forming reaction), and reacting it with chlorine in the presence of a particular solvent(chlorination reaction).

Typical reactions are:

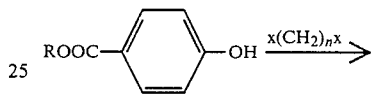

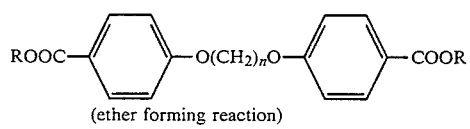
(ether forming reaction)

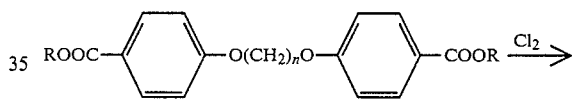

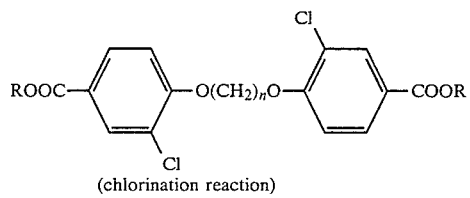
(chlorination reaction)

DISCLOSURE OF THE INVENTION

The present invention is a process for preparing α,ω-bis(2-chlorophenoxy)alkane-4,4'-dicarboxylic acid or its lower alkyl ester which comprises reacting α,ω-bis(phenoxy)alkane-4,4'-dicarboxylic acid or its lower alkyl ester with chlorine in the presence of a solvent selected from the group consisting (a) lower fatty acid having 2 to 6 carbon atoms, (b) hydrocarbon chloride having 1 to 8 carbon atoms, and (c) carbon chloride having 1 to 2 carbon atoms, in the absence or presence of a catalyst at a lower temperature than boiling point of said solvent.

Furthermore, the present invention is a process wherein α,ω-bis(phenoxy)alkane-4,4'-dicarboxylic acid or its lower alkyl ester obtained by heating p-hydroxybenzoic acid or its lower alkyl ester with alkylene dichloride is used as a starting material.

In general, when a complicated compound having a high molecular weight is chlorinated, many by-products are produced lowering the purity or yield of the product, since the complicated compound has various positions capable of being chlorinated. Therefore the chlorination reaction is usually carried out in a simple compound having a low molecular weight, prior to the other reaction.

However, in the present invention, it has found that α,ω-bis(2-chlorophenoxy)alkane-4,4'-dicarboxylic acid or its lower alkyl ester can be prepared by selective mono-chlorination in the ortho-position to the neighboring oxygen atom of the aromatic ring of the α,ω-bis(-phenoxy)alkane-4,4'-dicarboxylic acid or its lower alkyl ester.

PREFERRED EMBODIMENT OF THE INVENTION

Hereinafter, the present invention is described in detail.

α,ω-bis(phenoxy)alkane-4,4'-dicarboxylic acid or its lower alkyl ester, prepared by various methods, may be used as a starting material.

A preferable method for preparation is the reaction of p-hydroxybenzoic acid or its lower alkyl ester with alkylene dichloride. p-Hydroxybenzoic acids or their lower alkyl esters, used in this reaction include, for example, p-hydroxybenzoic acid, methyl p-hydroxybenzoate, ethyl p-hydroxybenzoate, propyl p-hydroxybenzoate, butyl p-hydroxybenzoate, and the like. Among them, p-hydroxybenzoic acid or its methyl ester may be preferably used.

As alkylene dichloride, α,ω-dichloro polymethylene dichloride having 1 to 6 carbon atoms may be used. Alkylene dichlorides include, for example, ethylene dichloride, butylene dichloride, hexamethylene dichloride, and the like. Among them, ethylene dichloride may be preferably used. The amount of alkylene dichloride may be about 0.5 to 1.5 times the molar amount of p-hydroxybenzoic acid or its lower alkyl ester.

The reaction of p-hydroxybenzoic acid or its lower alkyl ester and alkylene dichloride may be carried out at a temperature in the range of about 80° to about 200° C. The reaction may be carried out either at atmospheric pressure or at stressed pressure, preferably at stressed pressure. Thus obtained α,ω-bis(phenoxy)alkane-4,4'-dicarboxylic acid or its ester may be isolated and purified for example, by cooling the reaction mixture, filtrating the deposited crystal, and washing it with lower alcohol or water.

α,ω-bis(phenoxy)alkane-4,4'-dicarboxylic acids or their lower alkyl esters, used as a starting material, include, for example, 1,2-bis(phenoxy)ethane-4,4'-dicarboxylic acid, 1,4-bis(phenoxy)butane-4,4'-dicarboxylic acid, 1,6-bis(phenoxy)hexane-4,4'-dicarboxylic acid, and their dimethyl ester, diethyl ester, dipropyl ester, and dibutyl ester and the like. Dimethyl, diethyl, dipropyl, dibutyl ester of 1,2-bis(phenoxy)ethane-4,4'-dicarboxylic acid; dimethyl, diethyl, dipropyl, dibutyl ester of 1,4-bis(phenoxy)butane-4,4'-dicarboxylic acid; dimethyl, diethyl, dipropyl, dibutyl ester of 1,6-bis(-phenoxy)hexane-4,4'-dicarboxylic acid, may be preferably used. In particular dimethyl 1,2-bis(phenoxy)ethane-4,4'-dicarboxylate is most preferably used.

Lower fatty acids having 2 to 4 carbon atoms used as a solvent include, for example, acetic acid, propionic acid, butanoic acid, and the like. Among them, acetic acid may be most preferably used.

Hydrocarbon halides and carbon halides used as a solvent include, for example, chlorobenzene, chlorotoluene, chloroxylene, dichlorobenzene, dichlorotoluene, trichlorobenzene, trichlorotoluene, carbon tetra-chloride, hexachloroethane, chloroform, dichloroethane, trichloroethane, tetrachloroethane, and the like. More than two solvents may be simultaneously used. Among them, chlorobenzene, dichlorobenzene and tetrachloroethane may be preferably used, and in particular dichlorobenzene (especially ortho-dichlorobenzene) or 1,1,2,2-tetrachloroethane may be most preferably used.

In the above mentioned reaction, a 2 to 4 mole ratio of chlorine/dicarboxylic acid or its lower ester of starting material, may be preferably employed, especially preferably 2 to 3.5.

The reaction was carried out by firstly dissolving the dicarboxylic acid or its ester in the above mentioned solvent to obtain the solution, and then blowing the chlorine gas through the solution. The reaction temperature may be employed below the boiling point. In particular a range of 90° to 140° C. may be suitable employed, when acetic acid, o-dichlorobenzene, or 1,1,2,2-tetrachloroethane, and the like that is preferable solvent in the present invention is used.

The solvent is required in an amount to dissolve the dicarboxylic acid or its ester of the starting material. For example, when dimethyl 1,2-bis(phenoxy)ethane-4,4'-dicarboxylate is employed as a starting material, the amount of acetic acid may be more than about 3 times, preferably 4 to 10 times, and the amount of ortho-chlorobenzene may be more than 1 times, preferably 2 to 15 times, and the amount of tetrachloroethane may be more than 1 times, preferably 1 to 9 times.

Still, when carbonchloride or hydrocarbon chloride is employed as a solvent, in the above mentioned reaction, Lewis acid, especially boron trifluoride, iodide, sulfuric acid, more preferably iodide may be added as a catalyst. By the addition, the yield improves.

The reaction may be carried out at any pressure including atmospheric pressure, or stressed pressure, reduced pressure. For industrial use, atmospheric pressure or slightly stressed pressure may be preferably employed.

The reaction may be carried out batchwise, continously or semicontinously.

α,ω-bis(2-chlorophenoxy)alkane-4,4'-dicarboxylic acid or its ester, the objective of the present invention, is efficiently obtained in high yield by cooling the reaction mixture after chlorination and filtering the product or by pouring the reaction mixture into a large quantity of water, filterating the precipitate, washing, and drying.

Moreover, the crystal of α,ω-bis(2-chlorophenoxy)alkane-4,4'-dicarboxylic acid or its ester obtained by the present invention, were white. The prior art had the following defect. That is, the crystals of α,ω-bis(2-chlorophenoxy)alkane-4,4'-dicarboxylic acid or its ester obtained by the prior art was coloured yellow because of a slight amount of coloured impurities which, could not be removed by the usual purification techniques (For example, a polymer colored brown was obtained by the polymerization reaction of this dicarboxylic or its ester and alkylene glycol). In present invention, the white crystals, not coloured yellow, can be obtained.

This invention will be more clearly understood by the following examples.

In the examples, all parts are by weight, and b-values are units to denote the yellowish degree (the higher the b-value is, the more yellowish the crystals and the like are), as measured by Sand M Colour Computer produced by Suga Shikenki Co.

EXAMPLE 1

Into a vessel equipped with a reflux condenser, were charged 50 g (0.15 mole) of dimethyl 1,2-bis(phenoxy)ethane-4,4'-dicarboxylate and 450 g of acetic acid. Then, the temperature of the reaction vessel was raised to 95° to 105° C. with stirring.

After dimethyl 1,2-bis(phenoxy)ethane-4,4'-dicarboxylate was completely dissolved, the reaction mixture was maintained at the same temperature with introducing 23 g (0.33 mole) of the chlorine gas into the reaction vessel for two hours.

Thereafter, the reaction mixture was cooled to the room temperature. The white precipitates formed were filtered off and dried. The yield of this white precipitates was 90%.

The melting point of the compound purified by recrystallization from toluene was 204° to 206° C., and the colour tone (b value) was 2.1, which was excellent (the recrystallization yield was 92%).

Thus obtained compound was confirmed to be dimethyl 1,2-bis(2-chlorophenoxy)ethane-4,4'-dicarboxylate, the objective by the elemental analysis as shown in Table 1.

TABLE 1

|    | Found (%) | Calculated (%) |
|----|-----------|----------------|
| C  | 54.2      | 54.1           |
| H  | 4.1       | 4.0            |
| Cl | 17.7      | 17.8           |

COMPARATIVE EXAMPLE 1

93 g (0.5 mole) of methyl 3-chloro-4-hydroxybenzoate and 27 g (0.5 mole) of sodium methylate were dissolved in 600 g of methanol. 25 g (0.25 mole) of ethylenedichloride was added to this solution, and then the reaction mixture was maintained with stirring at 150° C. for 6 hours in a 1 liter autoclave.

Thereafter, the reaction mixture was poured into the large quantity of water. The yellow precipitates formed were filtered off and dried.

The melting point of the obtained dimethyl 1,2-bis(2-chlorophenoxy)ethane-4,4'-dicarboxylate was 192° to 195° C., and the yield was 34%, which was extremely low. The colour tone (b value) was 8.7, which was inferior.

EXAMPLE 2

Into a vessel equipped with a reflux condenser, were charged 50 g (0.15 mole) of dimethyl 1,2-bis(phenoxy)ethane-4,4'-dicarboxylate and 1000 g of propionic acid. Then, the temperature of the reaction vessel was raised to 115° to 118° C. with stirring.

After dimethyl 1,2-bis(phenoxy)ethane-4,4'-dicarboxylate was completely dissolved, the reaction mixture was maintained at the same temperature with introducing 23 g (0.33 mole) of the chlorine gas into the reaction vessel for 2 hours.

Thereafter, the reaction mixture was poured into the large quantity of water. The white precipitates formed were filtered off and dried. The yield of this white precipitates was 80%.

The melting point of the compound purified by recrystallization from xylene was 203° to 205° C., and the colour tone (b value) was 2.0, which was excellent (the recrystallization yield was 92%).

Thus obtained compound was confirmed to be dimethyl 1,2-bis(2-chlorophenoxy)ethane-4,4'-dicarboxylate, the objective by the elemental analysis as shown in Table 2.

TABLE 2

|    | Found (%) | Calculated (%) |
|----|-----------|----------------|
| C  | 54.3      | 54.1           |
| H  | 4.2       | 4.0            |
| Cl | 17.6      | 17.8           |

EXAMPLE 3

Into a vessel equipped with a reflux condenser, were charged 50 g (0.15 mole) of dimethyl 1,2-bis(phenoxy)ethane-4,4'-dicarboxylate, 150 g of tetrachloromethane, and 0.2 g of iodine. Then, the temperature of the reaction vessel was raised to 110° C. with stirring.

After dimethyl 1,2-bis(phenoxy)ethane-4,4'-dicarboxylate was completely dissolved, the reaction mixture was maintained at the same temperature with introducing 27 g (0.38 mole) of the chlorine gas into the reaction vessel for 2 hours.

Thereafter, the reaction mixture was cooled. The white precipitates formed were filterated off and dried. The yield of this white precipitates was 91%.

The melting point of the compound purified by recrystallization from toluene was 204° to 205° C., and the colour tone (b value) was 2.2, which was excellent (the recrystallization yield was 90%).

Thus obtained compound was confirmed to be dimethyl 1,2-bis(2-chlorophenoxy)ethane-4,4'-dicarboxylate, the objective by the elemental analysis as shown in Table 3.

TABLE 3

|    | Found (%) | Calculated (%) |
|----|-----------|----------------|
| C  | 54.3      | 54.1           |
| H  | 4.0       | 4.0            |
| Cl | 17.6      | 17.8           |

EXAMPLE 4

Into a vessel equipped with a reflux condenser, were charged 50 g (0.15 mole) of dimethyl 1,2-bis(phenoxy)ethane-4,4'-dicarboxylate, 100 g of ortho-dichlorobenzene, and 0.2 g of iodine. Then, the temperature of the reaction vessel was raised to 130° C. with stirring.

After dimethyl 1,2-bis(phenoxy)ethane-4,4'-dicarboxylate was completely dissolved, the reaction mixture was maintained at the same temperature with introducing 27 g (0.38 mole) of the colorine gas into the reaction vessel.

Thereafter, the reaction mixture was cooled. The white precipitates formed were filterated off and dried. The yield of this white precipitates was 70%.

The melting point of the compound purified by recrystallization from toluene was 200° to 203° C., and the colour tone (b value) was 2.2, which was excellent (the recrystallization yield was 91%).

Thus obtained compound was confirmed to be dimethyl 1,2-bis(chlorophenoxy)ethane-4,4'-dicarboxylate, the objective by the elemental analysis as shown in Table 4.

TABLE 4

|    | Found (%) | Calculated (%) |
|----|-----------|----------------|
| C  | 54.0      | 54.1           |
| H  | 4.1       | 4.0            |
| Cl | 18.0      | 17.8           |

EXAMPLE 5

Into a vessel equipped with a reflux condenser, were charged 54 g (0.15 mole) of diethyl 1,2-bis(phenoxy)ethane-4,4'-dicarboxylate, 216 g of tetrachloroethane, and 0.2 g of iodine. Then, the temperature of the reaction vessel was raised to 105° to 115° C. with stirring.

Further, the reaction mixture was maintained with introducing 27 g (0.38 mole) of the chlorine gas into the reaction vessel by the similar manner to Example 1.

Thereafter, the reaction mixture was cooled. The white precipitates formed were filterated and dried. The yield of this white precipitates was 86%.

The melting point of the compound purified by recrystallization from xylene was 149° to 153° C., and the colour tone (b value) was 2.0, which was excellent (the recrystallization yield was 91%).

Thus obtained compound was confirmed to be diethyl 1,2-bis(2-chlorophenoxy)ethane-4,4'-dicarboxylate, the objective by the elemental analysis as shown in Table 5.

TABLE 5

|    | Found (%) | Calculated (%) |
|----|-----------|----------------|
| C  | 56.1      | 56.2           |
| H  | 4.5       | 4.7            |
| Cl | 16.8      | 16.6           |

EXAMPLE 6

Into a vessel equipped with a reflux condenser, were charged 54 g (0.15 mole) of dimethyl 1,4-bis(phenoxy)butane-4,4'-dicarboxylate, and 450 g of acetic acid. Then, the temperature of the reaction vessel was raised to 115° to 120° C. with stirring.

Afterwords, the reaction was conducted with introducing 23 g (0.33 mole) of the chlorine gas into the reaction vessel by the similar manner to Example 1.

Thereafter, the reaction mixture was poured into the large quantity of water. The white precipitates formed were filterated and dried. The yield of this white precipitates was 85%.

The melting point of the compound purified by recrystallization from ethyl acetate was 172° to 174° C., and the colour tone (b value) was 2.4, which was excellent (the recrystallization yield was 84%).

Thus obtained compound was confirmed to be dimethyl 1,4-bis(2-chlorophenoxy)butane-4,4-dicarboxylate the objective by the elemental analysis as shown in Table 6.

TABLE 6

|    | Found (%) | Calculated (%) |
|----|-----------|----------------|
| C  | 56.1      | 56.2           |
| H  | 4.6       | 4.7            |
| Cl | 16.7      | 16.6           |

EXAMPLE 7

Into a vessel equipped with a reflux condenser, were poured 54 g (0.15 mole) of dimethyl 1,4-bis(phenoxy)butane-4,4'-dicarboxylate, 100 g of ortho-dichlorobenzene, and 0.2 g of iodine. Then, the temperature of the reaction vessel was raised to 130° C. with stirring.

Further, the reaction was conducted with introducing 27 g (0.38 mole) of the chlorine gas into the reaction vessel by the similar manner to Example 1.

Thereafter, the reaction mixture was cooled. The white precipitates formed were filterated off and dried. The yield of this white precipitates was 80%.

The melting point of the compound purified by recrystallization from ethyl acetate was 174° to 176° C., and the colour tone (b value) was 2.7, which was excellent (the recrystallization yield was 84%).

Thus obtained compound was confirmed to be dimethyl 1,4-bis(2-chlorophenoxy)butane-4,4'-dicarboxylate, the objective by the elemental analysis as shown in Table 7.

TABLE 7

|    | Found (%) | Calculated (%) |
|----|-----------|----------------|
| C  | 56.0      | 56.2           |
| H  | 4.6       | 4.7            |
| Cl | 16.9      | 16.6           |

EXAMPLE 8

Into a vessel equipped with a reflux condenser, were charged 58 g (0.15 mole) of 1,6-bis(phenoxy)hexane-4,4'-dicarboxylate, 2,000 g of carbon tetrachloride, and 0.2 g of iodine. Then, the temperature of the reaction vessel was raised to 60° C. with stirring.

Further, the reaction mixture was maintained with introducing 27 g (0.38 mole) of the chloride gas into the reaction vessel by the similar manner to the Example 1.

Thereafter, the reaction mixture was cooled. The white precipitates formed were filterated and dried. The yield of this white precipitates was 72%.

The melting point of the compound purified by recrystallization from ethanol was 82° to 84° C., and the colour tone (b value) was 2.6, which was excellent.

Thus obtained compound was confirmed to be dimethyl 1,6-bis(2-chlorophenoxy)hexane-4,4'-dicarboxylate, the objective by the elemental analysis as shown in Table 8.

TABLE 8

|    | Found (%) | Calculated (%) |
|----|-----------|----------------|
| C  | 49.9      | 50.4           |
| H  | 4.0       | 4.2            |
| Cl | 27.7      | 27.1           |

EXAMPLE 9

348 g (2 mole) of sodium salt of methyl 4-hydroxybenzoate was added to 300 g of methanol. Then, 200 g (2 mole) of ethylenedichloride was added to the solution and the reaction mixture was maintained with stirring at 180° C. for 4 hours in 5 liter autoclave.

Thereafter, the reaction mixture was charged into the large quantity of water. The white precipitates formed were filterated off and dried. The yield of the crude dimethyl 1,2-bis(2-henoxyl)ethane-4,4'-dicarboxylate was 62%.

Into a vessel equipped with a reflux condenser, were charged 100 g (0.3 mole) of thus obtained dimethyl 1,2-bis(phenoxy)ethane-4,4'-dicarboxylate and 1,000 g of acetic acid. Then, the reaction mixture was maintained in a similar manner to Example 1.

The crude dimethyl 1,2-bis(2-chlorophenoxy)ethane-4,4'-dicarboxylate was obtained (the yield was 93% and the melting point was 201° to 204° C.). The colour tone (b value) was 2.7, which was excellent. The total yield was 58%.

COMPARATIVE EXAMPLE 2

Into a vessel equipped with a reflux condenser, were charged 304 g (2 mole) of methyl 4-hydroxybenzoate and 800 g of acetic acid.

Then, methyl 4-hydroxybenzoate was completely dissolved, the reaction was conducted with introducing 156 g (2.2 mole) of the chlorine gas into the reaction vessel.

Thereafter, the reaction mixture was cooled to the room temperature and then charged into the large quantity of water. 276 g of the white precipitates formed were obtained (the yield was 74%).

The melting point of the compound purified by recrystallization from methanol-water solvent was 106°–108° C. (the recrystallization yield was 91%). The results of the elemental analysis of this compounds were well agreed with the calculated value of methyl 3-chloro-4-hydroxybenzoate.

The ether forming reaction mixture was maintained in a similar manner to Example 1, using thus obtained 93 g (0.5 mole) of methyl-3-chloro-4-hydroxybenzoate and ethylenedichloride.

The crude dimethyl 1,2-bis(2-chlorophenoxy)ethane-4,4'-dicarboxylate was obtained (the yield was 37% and the melting point was 193° to 197° C.). The colour tone (b value) was 8.4, which is yellow and inferior. The total yield was 25%.

When this Comparative Example 2 was compared with Example 9, in this Comparative Example 2, the total yield was lower, the colour tone of the obtained dimethyl 1,2-bis(2-chlorophenoxyethane)-4,4'-dicarboxylate was inferior and the melting point was lower.

EXAMPLE 10

Into 3 liter of the autoclave, 138 g (1 mole) of 4-hydroxybenzoic acid, 100 g (2.5 mole) of sodium hydroxide, 130 g (1.3 mole) of ethylene dichloride and 250 g of water. Then, the reaction mixture was stirred at 130° C. for 14 hours. The reaction mixture was cooled, and then dissolved in hot water, and then the pH was adjusted to 1.0 with 10% of hydrochloric acid.

The deposited precipitates were hot-filtered, washed with water, and dried. Thus, the crude 1,2-bis(phenoxy)ethane-4,4'-dicarboxylic acid was obtained in a 73% yield.

600 g of methanol and 30 g of sulfuric acid were added to 151 g of thus obtained 1,2-bis(phenoxy)ethane-4,4'-dicarboxylic acid in 3 liter autoclave. The reaction mixture was maintained at 130° C. for 5 hours. Thus, dimethyl 1,2-bis(phenoxy)ethane-4,4'-dicarboxylate was obtained in a 81% yield.

The colour tone (b value) was 2.8, which was excellent, and the total yield was 54%.

COMPARATIVE EXAMPLE 3

Into a vessel equipped with a reflux condenser, were charged 138 g (1 mole) of 4-hydroxybenzoic acid and 1,500 g of acetic acid. After 4-hydroxybenzoic acid was completely dissolved, the reaction mixture was maintained with introducing 78 g (1.1 mole) of the chlorine gas into the reaction vessel for 6 hours.

Thereafter, the reaction mixture was cooled to room temperature and charged into the large quantity of water. The white precipitates formed were obtained (the yield was 76%).

This white precipitates was purified by recrystallization from methanol.

Into 1 liter autoclave were charged 86 g (0.5 mole) of thus obtained 3-chloro-4-hydroxybenzoic acid, 50 g (1.25 mole) of sodium hydroxide, 65 g (0.65 mole) of ethylene dichloride, and 125 g of water. Then, the reaction mixture was stirred at 130° C. for 14 hours.

The reaction mixture was cooled, and then dissolved in hot water, and then pH was adjusted to 1.0 with 10% of hydrochloric acid. The deposited precipitates were hot-filtered, washed with water, and dried. Thus, the crude 1,2-bis(phenoxy)ethane-4,4'-dicarboxylic acid was obtained in a 58% yield.

120 g of methanol and 6 g of sulfuric acid were added to 37 g of thus obtained dimethyl 1,2-bis(phenoxy)ethane-4,4'-dicarboxylate in 1 liter autoclave. The reaction mixture was maintained at 130° C. for 5 hours. Thus, dimethyl 1,2-bis(2-chlorophenoxy)ethane-4,4'-dicarboxylate was obtained in a 76% yield.

The colour tone (b value) was 7.9, which was yellow and inferior. The total yield was 29%. In this comparative Example, the total yield was lower, the colour tone of the obtained dimethyl 1,2-bis(chlorophenoxy)ethane-4,4'-dicarboxylate was inferior, and the melting point was lower than those in Example 10.

INDUSTRIAL UTILIZABILITY

α,ω-bis(2-chlorophenoxy)alkane-4,4'-dicarboxylic acid or its ester obtained in the present invention are useful for a material of high Young's modulus polyester, which can be applied to the reinforcing meterials for rubbers such as tire cords, conveyer belt, belts for power transmission.

We claim:

1. A process for preparing an α,ω-bis(2-chlorophenoxy)alkane-4,4'-dicarboxylic acid or its lower alkyl ester which comprises reacting an α,ω-bis(phenoxy)alkane-4,4'-dicarboxylic acid or its lower alkyl ester with chlorine in the presence of a solvent selected from the group consisting (a) lower fatty acid having 2 to 6 carbon atoms, (b) hydrocarbon chloride having 1 to 8 carbon atoms, and (c) carbon chloride having 1 to 2 carbon atoms, in the absence or presence of a catalyst at a temperature below the boiling point of said solvent.

2. A process for preparing an α,ω-bis(2-chlorophenoxy)alkane-4,4'-dicarboxylic acid or its lower alkyl ester which comprises:

(A) heating p-hydroxybenzoic acid or its lower alkyl ester with an alkylene dichloride, to obtain an α,ω-bis(phenoxy)alkane-4,4'-dicarboxylic acid or its lower alkyl ester; and (B) reacting said α,ω-bis(phenoxy)alkane-4,4'-dicarboxylic acid or its lower alkyl ester with chlorine in the presence of a solvent selected from the group consisting (a) lower fatty acid having 2 to 6 carbon atoms, (b) hydrocarbon chloride having 1 to 8 carbon atoms, and (c) carbon chloride having 1 to 2 carbon atoms, in the absence or presence of a catalyst at a temperature below the boiling point of said solvent.

3. A process according to claim 1 or 2, wherein the α,ω-bis(phenoxy)alkane-4,4'-dicarboxylic acid is 1,2-bis(phenoxy)ethane-4,4'-dicarboxylic acid dimethyl ester.

4. A process according to claim 1 or 2, wherein the lower fatty acid having 2 to 6 carbon atoms is acetic acid.

5. A process according to claim 1 or 2, wherein the hydrocarbon chloride having 1 to 8 carbon atoms is selected from the group consisting of chlorobenzene, dichlorobenzene, tetrachlorobenzene, and tetrachloroethane.

6. A process accoding to claim 1 or 2, wherein the carbon chloride having 1 to 2 carbon atoms is carbon tetrachloride.

7. A process according to claim 1 or 2, wherein the amount of chlorine is from about 2 to about 4 times the amount of the α,ω-bis(phenoxy)alkane-4,4'-dicarboxylic acid or its lower alkyl ester, by mole.

8. A process according to claim 1 or 2, wherein the solvent is selected from the group consisting of a hydrocarbon chloride having 1 to 8 carbon atoms and a carbon chloride having 1 to 2 carbon atoms, and wherein the catalyst is iodine.

* * * * *